United States Patent
Lutz et al.

(10) Patent No.: US 11,034,869 B2
(45) Date of Patent: Jun. 15, 2021

(54) ONE-COMPONENT TOUGHENED EPOXY ADHESIVES WITH IMPROVED ADHESION TO OILY SURFACES AND HIGH WASH-OFF RESISTANCE

(71) Applicant: DDP SPECIALTY ELECTRONIC MATERIALS US, LLC, Wilmington, DE (US)

(72) Inventors: Andreas Lutz, Freienbach (CH); Daniel Schneider, Freienbach (CH); Jeannine Flueckiger, Freienbach (CH)

(73) Assignee: DDP SPECIALTY ELECTRONIC MATERIALS US, LLC, Wilmington, DE (US)

( * ) Notice: Subject to any disclaimer, the term of this patent is extended or adjusted under 35 U.S.C. 154(b) by 0 days.

(21) Appl. No.: 16/936,628

(22) Filed: Jul. 23, 2020

(65) Prior Publication Data

US 2020/0347279 A1    Nov. 5, 2020

Related U.S. Application Data

(62) Division of application No. 15/757,877, filed as application No. PCT/US2016/050341 on Sep. 6, 2016, now abandoned.
(Continued)

(51) Int. Cl.
*C09J 163/04* (2006.01)
*C08G 59/40* (2006.01)
(Continued)

(52) U.S. Cl.
CPC .............. *C09J 163/04* (2013.01); *A61B 5/24* (2021.01); *A61B 5/296* (2021.01); *A61B 5/6877* (2013.01);
(Continued)

(58) Field of Classification Search
CPC ........ C09J 163/04; C09J 163/00; C09J 11/06; C08L 75/08; C08G 18/24; C08G 18/3215;
(Continued)

(56) References Cited

U.S. PATENT DOCUMENTS

| | | |
|---|---|---|
| 4,659,779 A | 4/1987 | Bagga et al. |
| 4,734,332 A | 3/1988 | Bagga et al. |

(Continued)

FOREIGN PATENT DOCUMENTS

| | | |
|---|---|---|
| EP | 1728825 | 12/2006 |
| EP | 1876194 | 1/2008 |

(Continued)

OTHER PUBLICATIONS

JP54-26000, Abstract.
JP1979026000; machine translation.

*Primary Examiner* — Daniel H Lee
(74) *Attorney, Agent, or Firm* — Hong Xu

(57) ABSTRACT

Epoxy adhesives include a latent curing agent, a reactive toughener having capped isocyanate groups, and certain urea compounds. The toughener is made by chain extending and capping a mixture of isocyanate-terminated prepolymers. The prepolymers include an isocyanate-terminated polyether and an isocyanate-terminated diene polymer. The adhesives have excellent wash-off resistance and excellent ability to adhere to oily substrates.

12 Claims, 2 Drawing Sheets

Related U.S. Application Data

(60) Provisional application No. 62/216,395, filed on Sep. 10, 2015.

(51) Int. Cl.

| | |
|---|---|
| *C08G 18/10* | (2006.01) |
| *C09J 163/00* | (2006.01) |
| *C08G 65/333* | (2006.01) |
| *C08G 18/80* | (2006.01) |
| *A61N 1/05* | (2006.01) |
| *C08G 59/68* | (2006.01) |
| *C08G 18/12* | (2006.01) |
| *C08G 18/48* | (2006.01) |
| *A61B 5/00* | (2006.01) |
| *C08G 18/69* | (2006.01) |
| *C08G 18/67* | (2006.01) |
| *C08L 75/08* | (2006.01) |
| *C08G 18/73* | (2006.01) |
| *A61B 5/24* | (2021.01) |
| *A61B 5/296* | (2021.01) |
| *C08G 18/24* | (2006.01) |
| *C08G 18/32* | (2006.01) |
| *C08G 18/62* | (2006.01) |
| *C08G 18/75* | (2006.01) |
| *C01B 32/182* | (2017.01) |

(52) U.S. Cl.
CPC .......... *A61B 5/6882* (2013.01); *A61N 1/0551* (2013.01); *C08G 18/10* (2013.01); *C08G 18/12* (2013.01); *C08G 18/24* (2013.01); *C08G 18/3215* (2013.01); *C08G 18/4854* (2013.01); *C08G 18/6204* (2013.01); *C08G 18/675* (2013.01); *C08G 18/698* (2013.01); *C08G 18/73* (2013.01); *C08G 18/755* (2013.01); *C08G 18/8067* (2013.01); *C08G 59/4021* (2013.01); *C08G 59/686* (2013.01); *C08G 65/33348* (2013.01); *C08L 75/08* (2013.01); *C09J 163/00* (2013.01); *A61B 2562/125* (2013.01); *A61N 1/0558* (2013.01); *C01B 32/182* (2017.08)

(58) Field of Classification Search
CPC .............. C08G 18/6204; C08G 18/755; C08G 65/33348; C08G 59/4021; C08G 18/10; C08G 18/8067; C08G 59/686; C08G 18/12; C08G 18/4854; C08G 18/698; C08G 18/675; C08G 18/73; A61N 1/0558; A61N 1/0551; C01B 32/182; A61B 5/24; A61B 5/296; A61B 5/6882; A61B 5/6877; A61B 2562/125

See application file for complete search history.

(56) References Cited

U.S. PATENT DOCUMENTS

| | | | |
|---|---|---|---|
| 5,112,932 A | 5/1992 | Koenig et al. | |
| 5,202,390 A | 4/1993 | Mulhaupt et al. | |
| 5,278,257 A | 1/1994 | Mulhaupt et al. | |
| 7,557,168 B2 | 7/2009 | Lutz et al. | |
| 7,615,595 B2 | 11/2009 | Lutz et al. | |
| 7,750,107 B2 | 7/2010 | Antelmann et al. | |
| 8,062,468 B2 | 11/2011 | Finter et al. | |
| 8,071,217 B2 | 12/2011 | Kramer et al. | |
| 8,076,424 B2 | 12/2011 | Kramer et al. | |
| 8,114,519 B2 | 2/2012 | Kramer et al. | |
| 8,202,920 B2 | 6/2012 | Kramer et al. | |
| 8,404,787 B2 | 3/2013 | Lutz et al. | |
| 8,608,899 B2 | 12/2013 | Kramer et al. | |
| 8,974,905 B2 | 3/2015 | Sang et al. | |
| 2005/0070634 A1 | 3/2005 | Lutz et al. | |
| 2005/0207401 A1 | 9/2005 | Gu et al. | |
| 2006/0276601 A1 | 12/2006 | Lutz et al. | |
| 2009/0264558 A1 | 10/2009 | Kramer et al. | |
| 2009/0324958 A1* | 12/2009 | Schulenburg | C08L 53/00 428/414 |
| 2010/0019539 A1 | 1/2010 | Nakamura et al. | |
| 2010/0273005 A1 | 10/2010 | Kramer et al. | |
| 2010/0310878 A1 | 12/2010 | Hofstetter et al. | |
| 2011/0067813 A1* | 3/2011 | Kramer | C08G 18/4045 156/330 |
| 2011/0130479 A1 | 6/2011 | Kramer et al. | |
| 2011/0215632 A1 | 9/2011 | Gleyal | |
| 2013/0090431 A1 | 4/2013 | Ming et al. | |
| 2013/0115442 A1* | 5/2013 | Sang | C08G 59/50 428/327 |
| 2016/0272750 A1 | 9/2016 | Voci et al. | |
| 2017/0022402 A1* | 1/2017 | Lutz | B05D 3/0272 |
| 2019/0002626 A1 | 1/2019 | Kramer et al. | |

FOREIGN PATENT DOCUMENTS

| | | |
|---|---|---|
| EP | 1916269 | 4/2008 |
| EP | 1916270 | 4/2008 |
| EP | 1916285 | 4/2008 |
| EP | 2128182 | 12/2009 |
| JP | 54-26000 | 2/1979 |
| JP | 1979026000 | 2/1979 |
| WO | 2005007766 | 1/2005 |
| WO | 2005070634 | 8/2005 |
| WO | 2005118734 | 12/2005 |
| WO | 2006128722 | 12/2006 |
| WO | 2009094295 | 7/2009 |
| WO | 2009095484 | 8/2009 |
| WO | 2012091842 | 7/2012 |
| WO | 2014072515 | 5/2014 |
| WO | 2014172444 | 10/2014 |

\* cited by examiner

ONE-COMPONENT TOUGHENED EPOXY ADHESIVES WITH IMPROVED ADHESION TO OILY SURFACES AND HIGH WASH-OFF RESISTANCE

This invention relates to one-component epoxy adhesives that contain an elastomeric toughener.

Toughened one-component epoxy adhesives are used extensively in the automotive and other industries for metal-metal bonding as well as bonding metals to other materials. These adhesives often contain "tougheners" that help the cured adhesive resist failure. The tougheners have blocked isocyanate groups that, under the conditions of the curing reaction, can become de-blocked and react with an epoxy resin. Tougheners of this type are described, for example, in U.S. Pat. Nos. 5,202,390, 5,278,257, WO 2005/118734, WO 2007/003650, WO2012/091842, U.S. Published Patent Application No. 2005/0070634, U.S. Published Patent Application No. 2005/0209401, U.S. Published Patent Application 2006/0276601, EP-A-0 308 664, EP1498441A, EP-A 1728825, EP-A 1 896 517, EP-A 1 916 269, EP-A 1 916 270, EP-A 1 916 272 and EP-A-1 916 285.

In many metal bonding applications, where one or both substrates are metals, the metal substrate to be bonded is contaminated with an oily material. The oil is often a lubricant or an anti-corrosion fluid. Anti-corrosion fluids are often applied to metal sheet by their manufacturers, to prevent surface corrosion from occurring until such later time as the metal is fabricated into some specific part or product, and/or until a protective coating is applied. Lubricants are commonly applied to metals when they are fabricated, such as by cutting, molding or stamping. The lubricants reduce wear on the metals and the tooling. There is a recent trend towards using higher viscosity oils for these purposes.

In specific manufacturing settings, this oil often remains on the metal at the time the adhesive is applied. When vehicle bodies are assembled, for example, it is often convenient to partially or fully assemble the vehicle body before removing the oil from the individual metal parts. This way, the partially or fully assembled body can be washed or "degreased" at once, rather than degreasing the separate components individually.

The presence of the oil creates two distinct problems.

The first problem has to do with the ability of the adhesive to adhere strongly to the substrate. The presence of an oily material on the substrate surface creates a physical barrier separating the adhesive and metal. If the adhesive is to adhere strongly to the metal, it is necessary that the adhesive overcome this barrier. This means the adhesive must be able to penetrate the oil while the adhesive is in an uncured or at most partially cured state, in effect removing the physical barrier between adhesive and substrate. This becomes more difficult as the viscosity of the oil increases. Current toughened epoxy adhesives often do not penetrate the oil as well as is needed.

The second problem arises in manufacturing processes in which the degreasing step is performed after the adhesive is applied but before it is cured. In such a case, the adhesive must withstand the degreasing process without being washed off. Wash-off resistance therefore, is an important attribute of adhesives that are used in these kinds of manufacturing processes. The problem becomes more difficult as the industry trends towards using higher viscosity oils. Higher viscosity oils often require higher degreasing temperatures. At these higher temperatures, the adhesive becomes more susceptible to being washed away.

Thus, a desirable toughened adhesive has the ability to bond to oily surfaces and in addition is resistant to being washed off. Such an adhesive must also perform adequately in terms of bond strength and impact resistance.

This invention is in one aspect a one-component epoxy adhesive comprising in admixture:

A) at least 25 weight percent, based on the weight of the adhesive, of one or more non-rubber-modified epoxy resins;
B) 5 to 45 weight percent, based on the weight of the composition, of a reactive elastomeric toughener having capped isocyanate groups, which reactive elastomeric toughener includes a chain-extended and then isocyanate-capped mixture of i) a 1000 to 10,000 number average molecular weight isocyanate-terminated polyether and ii) a 1000 to 10,000 number average molecular weight isocyanate-terminated diene polymer;
C) one or more latent epoxy curing agents in an amount sufficient to cure the adhesive; and
D) 0.1 to 3 weight percent, based on the weight of the adhesive, of at least one urea compound having one or more urea groups and a molecular weight per urea group of up to 250, the adhesive being devoid of an aminophenol curing accelerator.

Applicants have found that through the simultaneous selection of the specific toughener and the urea compound, an adhesive is produced that adheres very well to oily substrates. In addition, the adhesive has good wash-off resistance and cures to form an adhesive bond that has good lap shear strength and impact peel resistance.

The benefits of the invention are not obtained when the toughener is present without the urea compound, or when the urea compound is present together with various other tougheners. The selection of both together appears to be necessary.

The invention is also a method comprising forming a layer of the adhesive of the invention at a bondline between two substrates to form an assembly, and then curing the adhesive layer at the bondline to form an adhesive bond between the two substrates. At least one and preferably both of the members may be metals.

In a specific embodiment, the invention is a method for adhering a first oily substrate to a second substrate, comprising 1) forming a layer of the adhesive of any of claims 1-9 at a bondline between the first oily substrate and the second substrate to form an assembly that includes the first and second substrates each in contact with the adhesive composition at the bondline; then 2) degreasing the assembly to remove oil from the first oily substrate; and then 3) heating the degreased assembly to an elevated temperature to cure the adhesive.

Such a method may further comprise steps of

1-A): after step 1) and before step 2), fastening the assembly using mechanical means, by spot-curing one or more portions of the adhesive composition, or both, to maintain the substrates and adhesive in a fixed position relative to each other, wherein at least a portion of the adhesive remains uncured; and 2-A): after step 2) and before step 3), contacting the fastened assembly with a heat-curable coating to form a coated and fastened assembly. In this process, the coating and the adhesive are cured in step 3).

The invention is also reactive elastomeric toughener having capped isocyanate groups, which reactive elastomeric toughener includes a chain-extended and then isocyanate-capped mixture of i) a 1000 to 10,000 number average molecular weight isocyanate-terminated polyether and ii) a 1000 to 10,000 number average molecular weight isocyanate-terminated diene polymer.

The invention is in still another aspect an epoxy adhesive containing

A) at least 25 weight percent, based on the weight of the adhesive, of one or more non-rubber-modified epoxy resins;
B) 5 to 45 weight percent, based on the weight of the composition, of a reactive elastomeric toughener having capped isocyanate groups, which reactive elastomeric toughener includes a chain-extended and then isocyanate-capped mixture of i) a 1000 to 10,000 number average molecular weight isocyanate-terminated polyether and ii) a 1000 to 10,000 number average molecular weight isocyanate-terminated diene polymer;
C) one or more latent epoxy curing agents in an amount sufficient to cure the adhesive; and
D) 0.1 to 5 weight percent, based on the weight of the adhesive, of at least one urea compound having one or more urea groups and a molecular weight per urea group of up to 250,
the adhesive being devoid of an aminophenol curing accelerator.

Figure 1A:
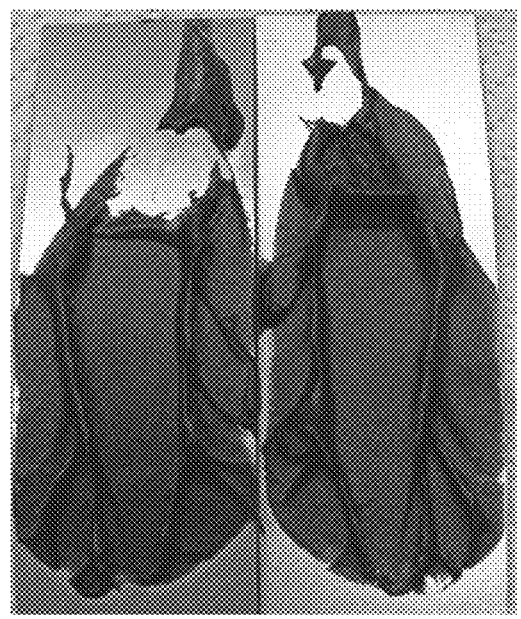
FIG. 1A is a photograph of separated oily metal substrates with applied adhesive of the invention, which demonstrates excellent performance on the tack test described below.

Suitable epoxy resins include those described at column 2, line 66 to column 4, line 24 of U.S. Pat. No. 4,734,332, incorporated herein by reference. The epoxy resin should have an average of at least 1.8 epoxide groups per molecule. The epoxy resin(s) are not rubber-modified, meaning that, prior to curing the adhesive, the epoxy resins are not chemically bonded to a rubber.

Suitable epoxy resins include diglycidyl ethers of polyhydric phenol compounds such as resorcinol, catechol, hydroquinone, biphenol, bisphenol A, bisphenol AP (1,1-bis(4-hydroxylphenyl)-1-phenyl ethane), bisphenol F, bisphenol K and tetramethylbiphenol; diglycidyl ethers of aliphatic glycols such as the diglycidyl ethers of $C_{2-24}$ alkylene glycols; polyglycidyl ethers of phenol-formaldehyde novolac resins (epoxy novolac resins), alkyl substituted phenol-formaldehyde resins, phenol-hydroxybenzaldehyde resins, cresol-hydroxybenzaldehyde resins, dicyclopentadiene-phenol resins and dicyclopentadiene-substituted phenol resins; cycloaliphatic epoxy resins, and any combination of any two or more thereof.

Suitable epoxy resins include diglycidyl ethers of bisphenol A resins such as are sold by The Dow Chemical Company under the designations D.E.R.® 330, D.E.R.® 331, D.E.R.® 332, D.E.R.® 383, D.E.R. 661 and D.E.R.® 662 resins.

Suitable epoxy novolac resins that are commercially available include those sold as D.E.N.® 354, D.E.N.® 431, D.E.N.® 438 and D.E.N.® 439 from The Dow Chemical Company.

Suitable cycloaliphatic epoxy resins include those described in U.S. Pat. No. 3,686,359, incorporated herein by reference. Cycloaliphatic epoxy resins of particular interest are (3,4-epoxycyclohexyl-methyl)-3,4-epoxy-cyclohexane carboxylate, bis-(3,4-epoxycyclohexyl) adipate, vinylcyclohexene monoxide and mixtures thereof.

Other suitable epoxy resins include oxazolidone-containing compounds as described in U.S. Pat. No. 5,112,932. In addition, an advanced epoxy-isocyanate copolymer such as those sold commercially as D.E.R. 592 and D.E.R. 6508 (Dow Chemical) can be used.

The epoxy resin preferably is one or more diglycidyl ethers of a polyhydric phenol or a mixture thereof with up to 10 percent by weight of another type of epoxy resin. The most preferred epoxy resins are diglycidyl ethers of bisphenol-A and diglycidyl ethers of bisphenol-F. These can have average epoxy equivalent weights of from about 170 to 600 or more, preferably from 225 to 400.

An especially preferred epoxy resin is a mixture of at least one diglycidyl ether of a polyhydric phenol, preferably bisphenol-A or bisphenol-F, having an epoxy equivalent weight of from 170 to 299, especially from 170 to 225, and at least one second diglycidyl ether of a polyhydric phenol, again preferably bisphenol-A or bisphenol-F, this one having an epoxy equivalent weight of at least 300, preferably from 310 to 600. The proportions of the resins are preferably such that the mixture has an average epoxy equivalent weight of from 225 to 400. The mixture optionally may also contain up to 20%, preferably up to 10%, of one or more other epoxy resins.

The epoxy resin preferably will constitute at least about 25 weight percent of the adhesive, more preferably at least about 30 weight percent, and still more preferably at least about 40 weight percent. The epoxy resin may constitute up to about 75 weight percent of the adhesive, more preferably up to about 60 weight percent.

In some embodiments, the adhesive composition contains 30 to 60, preferably 40 to 60, weight percent of a diglycidyl ether of bisphenol A that has an epoxy equivalent weight of up to 225, and 0 to 10%, preferably 2 to 6 weight percent, of a diglycidyl ether of bisphenol A that has an epoxy equivalent weight of 400 or greater, preferably 400 to 1500. Such an adhesive composition optionally contains 0.5 to 10 weight percent of a different epoxy resin such as an epoxy novolac resin or an epoxy cresol novolac resin.

The toughener is an elastomeric material that has terminal capped isocyanate groups. It is made in a process that includes the steps of chain-extending a mixture of isocyanate-terminated compounds and then capping the remaining isocyanate groups of the chain-extended material.

The isocyanate-terminated compounds include i) at least one 1000 to 10,000 number average molecular weight isocyanate-terminated polyether and ii) at least one 1000 to 10,000 number average molecular weight isocyanate-terminated diene polymer.

The polyether portion of the isocyanate-terminated polyether may be a polymer of one or more of tetrahydrofuran (tetramethylene oxide), 1,2-butylene oxide, 2,3-butylene oxide, 1,2-propylene oxide and ethylene oxide, with polymers or copolymers of at least 70 weight percent, based on the total weight of the polymer or copolymer, of tetrahydrofuran, 1,2 -butylene oxide, 2,3-butylene oxide and 1,2-propylene oxide being preferred. Polymers of at least 80 weight percent tetrahydrofuran, based on the total weight of the polymer or copolymer are especially preferred.

The isocyanate-terminated polyether is conveniently prepared by the reaction of an amine- or hydroxyl-terminated polyether with a polyisocyanate, at a ratio of at least 1.5 equivalents, preferably 1.8 to 2.5 equivalents or 1.9 to 2.2 equivalents, of polyisocyanate per equivalent of amine- and/or hydroxyl groups on the starting polyether. The starting polyether preferably has 2 to 3, more preferably 2, amine and or hydroxyl groups per molecule. The polyisocyanate preferably has 2 isocyanate groups per molecule. The isocyanate-terminated polyether preferably has 2 to 3, more preferably 2, isocyanate groups per molecule. The starting polyether preferably has a number average molecular weight of 900 to 800, more preferably 1500 to 6000 or 1500 to 4000. The polyisocyanate preferably has a molecular weight of up to 300.

The isocyanate-terminated diene polymer is conveniently prepared by the reaction of an amine- or hydroxyl-terminated diene polymer with a polyisocyanate, at a ratio of at least 1.5 equivalents, preferably 1.8 to 2.5 equivalents or 1.9 to 2.2 equivalents, of polyisocyanate per equivalent of amine- and/or hydroxyl groups on the starting diene polymer.

The starting diene polymer preferably has a glass transition temperature, prior to reaction with the polyisocyanate, of no greater than −20° C. and preferably no greater than −40° C. The diene polymer is a liquid homopolymer or copolymer of a conjugated diene, especially a diene/nitrile copolymer. The conjugated diene is preferably butadiene or isoprene, with butadiene being especially preferred. The preferred nitrile monomer is acrylonitrile. Preferred copolymers are butadiene-acrylonitrile copolymers. The rubbers preferably contain, in the aggregate, no more than 30 weight percent polymerized unsaturated nitrile monomer, and preferably no more than about 26 weight percent polymerized nitrile monomer.

The starting diene polymer preferably has 2 to 3, more preferably 2, amine and/or hydroxyl groups per molecule. The polyisocyanate preferably has 2 isocyanate groups per molecule. The isocyanate-terminated diene polymer preferably has 2 to 3, more preferably 2, isocyanate groups per molecule. The starting diene polymer preferably has a number average molecular weight of 900 to 800, more preferably 1500 to 6000 and still more preferably 2000 to 3000. The polyisocyanate preferably has a molecular weight of up to 300.

The isocyanate-terminated polyether and isocyanate-terminated diene polymer can have aromatic isocyanate groups, but the isocyanate groups are preferably aliphatic. When the isocyanate-terminated polymers are made in the process described above, the polyisocyanate may be an aromatic polyisocyanate, but it is preferably an aliphatic polyisocyanate such as isophorone diisocyanate, 1,6-hexamethylene diisocyanate, hydrogenated toluene diisocyanate, hydrogenated methylene diphenylisocyanate ($H_{12}$MDI), and the like.

The isocyanate-terminated polyether and isocyanate-terminated diene polymer may be made separately and then blended. Alternatively, they are made simultaneously by blending an amine- or hydroxyl-terminated polyether and an amine- or hydroxyl-terminated diene polymer, each as described above, and reacting the blended materials with a polyisocyanate to form the mixture of isocyanate-terminated species directly.

The weight ratio of isocyanate-terminated polyether and isocyanate-terminated diene polymer may be, for example, about 5:95 to 95:5. A preferred weight ratio is about 50:50 to 95:5 and a more preferred ratio is about 70:30 to 90:10.

The reaction to form the isocyanate-terminated polymers can be performed by combining the materials in the stated ratios and heating to 60 to 120° C., optionally in the presence of a catalyst for the reaction of isocyanate groups with the isocyanate-reactive groups of the polyether or diene polymer. The reaction is continued until the isocyanate content is reduced to a constant value, or to a target value, or until the amine-and or hydroxyl groups of the starting polyether or diene polymer are consumed.

If desired, branching can be introduced into the isocyanate-terminated polyether and/or isocyanate-terminated diene polymer. When they are made a process such as described before, this can be done by adding branching agent into the reaction between the polymeric starting materials and the polyisocyanate. The branching agent, for purposes of this invention, is a polyol or polyamine compound having a molecular weight of up to 599, preferably from 50 to 500, and at least three hydroxyl, primary amino and/or secondary amino groups per molecule. If used at all, branching agents generally constitute no more than 10%, preferably no more than 5% and still more preferably no more than 2% of the combined weight of the branching agent and the starting polymer (i.e., the amine- or hydroxyl-terminated polyether or diene polymer). Examples of branching agents include polyols such as trimethylolpropane, glycerin, trimethylolethane, ethylene glycol, diethylene glycol, propylene glycol, dipropylene glycol, sucrose, sorbitol, pentaerythritol, triethanolamine, diethanolamine and the like, as well as alkoxylates thereof having a number average molecular weight of up to 599, especially up to 500.

The mixture of isocyanate-terminated polyether and isocyanate-terminated diene polymer is chain extended to produce a chain extended, isocyanate-terminated prepolymer. Chain extenders include polyol or polyamine compounds having a molecular weight of up to 749, preferably from 50 to 500, and two hydroxyl, primary amino and/or secondary amino groups per molecule. Examples of suitable chain extenders include aliphatic diols such as ethylene glycol, diethylene glycol, triethylene glycol, propylene glycol, dipropylene glycol, tripropylene glycol, 1,4-butanediol, 1,6-hexane diol, cyclohexanedimethanol and the like; aliphatic or aromatic diamines such as ethylene diamine, piperazine, aminoethylpiperazine, phenylene diamine, diethyltoluenediamine and the like, and compounds having two phenolic hydroxyl groups such resorcinol, catechol, hydroquinone, bisphenol, bisphenol A, bisphenol AP (1,1-bis(4-hydroxylphenyl)-1-phenyl ethane), bisphenol F, bisphenol K, bisphenol M, tetramethylbiphenol and o,o'-diallyl-bisphenol A, and the like. Among these, the compounds having two phenolic hydroxyl groups are preferred.

The chain extension reaction is performed in the same general manner as the prepolymer-forming reaction. Enough of the prepolymers are mixed with the chain extender to provide at least two equivalents of isocyanate groups per equivalent of isocyanate-reactive groups contributed by the chain extender. 1.5 to 4 or more, preferably 1.75 to 3 and more preferably 1.8 to 2.5 equivalents of isocyanate groups may be provided per equivalent of isocyanate-reactive groups contributed by the chain extender during the chain extension reaction.

The chain extension reaction is performed by combining the mixture of isocyanate-terminated polyether and isocyanate-terminated diene polymer with the chain extender, and subjecting the mixture to conditions under which the isocyanate-reactive groups of the chain extender react isocyanate groups of the isocyanate-terminated materials to form the chain-extended prepolymer.

The chain-extended prepolymer will be a mixture of materials. It will consist mainly of isocyanate-terminated polymers that correspond to two or more of the starting isocyanate-terminated polymers coupled together by residue(s) of the chain extender. A portion of the prepolymer molecules will have two or more polyether chains, corresponding to the polyether chains of the isocyanate-terminated polyether. A portion of the prepolymer molecules will have one or more polyether chains, corresponding to the polyether chains of the isocyanate-terminated polyether, and one or more diene polymer chains, corresponding to the diene polymer chains of the isocyanate-terminated diene polymer. There may be prepolymer molecules that having two more diene polymer chains, corresponding to the diene polymer chains of the isocyanate-terminated diene polymer. The chain-extended prepolymer may contain small quantities of unreacted starting materials, and/or of reaction products of one molecule of chain extender with only one molecule of isocyanate-terminated polyether or isocyanate-terminated diene polymer.

Conditions for the chain-extension reaction are generally as described with respect to the reaction of the amine- or hydroxyl-terminated polymer with the polyisocyanate.

The isocyanate groups of the chain-extended prepolymer are then capped by reaction with a capping group. Various types of capping groups are suitable including those described in U.S. Pat. Nos. 5,202,390, 5,278,257, 7,615,595, US Published Patent Application Nos. 2005-0070634, 2005-0209401, 2006-0276601 and 2010-0019539, WO 2006/128722, WO 2005/118734 and WO 2005/0070634, all incorporated herein by reference. Among the useful capping agents are:

a) Aliphatic, aromatic, cycloaliphatic, araliphatic and/or heteroaromatic monoamines that have one primary or secondary amino group. Examples of such capping compounds include monoalkyl amines such as methyl amine, ethyl amine, isopropyl amine, sec-butylamine, t-butyl amine; dialkyl amines such as dimethylamine, diethylamine, diisopropylamine, di-sec-butylamine, dihexylamine and dioctyl amine; cyclohexylamine or dicyclohexylamine wherein the cyclohexyl groups are optionally substituted with one or more alkyl groups; benzylamine and diphenylamine wherein the phenyl groups are optionally substituted with one or more alkyl groups; morpholine; N-alkylpiperadines and imidazols having an amine hydrogen atom.

b) phenolic compounds, including monophenols, polyphenols and aminophenols. Examples of monophenols include phenol, alkyl phenols that contain one or more alkyl groups that each may contain from 1 to 30 carbon atoms, naphthol, a halogenated phenol, cardanol, or naphthol. Suitable polyphenols contain two or more, preferably two, phenolic hydroxyl groups per molecule and include resorcinol, catechol, hydroquinone, bisphenol, bisphenol A, bisphenol AP (1,1-bis(4-hydroxylphenyl)-1-phenyl ethane), bisphenol F, bisphenol K, bisphenol M, tetramethylbiphenol and o,o'-diallyl-bisphenol A, as well as halogenated derivatives thereof. Suitable aminophenols are compounds that contain at least one primary or secondary amino group and one phenolic hydroxyl group. The amino group is preferably bound to a carbon atom of an aromatic ring. Examples of suitable aminophenols include 2- aminophenol, 4-aminophenol, various aminonaphthols, and the like. Among the phenolic compounds, the monophenols and aminophenols are generally preferred.

c) Benzyl alcohol, which may be substituted with one or more alkyl groups on the aromatic ring;

d) Hydroxy-functional acrylate or methacrylate compounds such as 2-hydroxyethylacrylate, 2-hydroxypropylacrylate, 4-hydroxybutylacrylate, 2-hydroxy-butylacrylate, 2- aminopropylacrylate, 2-hydroxyethylmethacrylate, 2-hydroxypropyl-methacrylate, 4-hydroxybutylmethacrylate and 2 -hydroxybutylmethacrylate;

e) thiol compounds such as alkylthiols having 2 to 30, preferably 6 to 16, carbon atoms in the alkyl group, including dodecanethiol;

f) alkyl amide compounds having at least one amine hydrogen such as acetamide and N-alkylacetamide; and g) a ketoxime.

The monophenol and aminophenol capping agents are generally preferable. In some embodiments, at least 90%, preferably at least 95%, more preferably at least 98%, up to 100% of the isocyanate groups of the prepolymer are capped with capping agents of one or more of these types. In such embodiments any remaining uncapped isocyanate groups may be capped with another type of capping agent.

The capping reaction can be performed under the general conditions described already, i.e., by combining the materials in the stated ratios and allowing them to react at room temperature or an elevated temperature such as 60 to 120° C., optionally in the presence of a catalyst for the reaction of isocyanate groups with the isocyanate-reactive groups of the capping agent. The reaction is continued until the isocyanate content is reduced to a constant value, which is preferably less than 0.1% by weight. Fewer than 3%, preferably fewer than 1%, of the isocyanate groups may remain uncapped.

The resulting toughener suitably has a number average molecular weight of at least 3000, preferably at least 4,000, to about 35,000, preferably to about 20,000 and more preferably to about 15,000, as measured by GPC, taking into account only those peaks that represent molecular weights of 1000 or more.

The polydispersity (ratio of weight average molecular weight to number average molecular weight) of the toughener is suitably from about 1 to about 4, preferably from about 1.5 to 2.5. The toughener suitably contains, on average, from about 1.5, preferably from about 2.0, to about 6, preferably to about 4, more preferably to about 3 and still more preferably to about 2.5, capped isocyanate groups per molecule. An especially preferred prepolymer contains an average of from 1.9 to 2.2 capped isocyanate groups per molecule.

The toughener should constitute at least 5 weight percent of the adhesive composition. The amount of toughener may be at least 8 weight percent or at least 10 weight percent. The toughener may constitute up to 45 weight percent thereof, preferably up to 30 weight percent and more preferably up to 25 weight percent.

The adhesive also contains a latent curing agent. A curing agent is consider to be "latent" for purposes of this invention if the adhesive, including components A)-D) as set forth above, exhibits a curing temperature of at least 60° C. The curing temperature preferably is at least 80° C., and may be at least 100° C. or at least 140° C. It may be as high as, for example, 180° C. The "curing temperature" refers to the lowest temperature at which the structural adhesive achieves at least 30% of its lap shear strength (DIN ISO 1465) at full cure within 2 hours. The lap shear strength at "full cure" is measured on a sample that has been cured for 30 minutes at 180° C., which conditions represent "full cure" conditions.

Suitable latent curing agents include materials such as boron trichloride/amine and boron trifluoride/amine complexes, melamine, diallylmelamine, guanamines such as dicyandiamide, methyl guanidine, dimethyl guanidine, trimethyl guanidine, tetramethyl guanidine, methylisobiguanidine, dimethylisobiguanidine, tetramethylisbiguandidine, heptamethylisobiguanidine, hexamethylisobiguanidine, acetoguanamine and benzoguanamine, aminotriazoles such as 3-amino-1,2,4-triazole, hydrazides such as adipic dihydrazide, stearic dihydrazide, isophthalic dihydrazide, semicarbazide, cyanoacetamide, and aromatic polyamines such as diaminodiphenylsulphones. Dicyandiamide is a particularly preferred curing agent.

The latent curing agent is used in an amount sufficient to cure the adhesive. Typically, enough of the curing agent is provided to consume at least 80% of the epoxide groups present in the composition. A large excess over that amount needed to consume all of the epoxide groups is generally not needed. Preferably, the curing agent constitutes at least about 1.5 weight percent of the adhesive, more preferably at least about 2.5 weight percent and even more preferably at least 3.0 weight percent thereof. The curing agent preferably constitutes up to about 15 weight percent of the adhesive composition, more preferably up to about 10 weight percent, and most preferably up to about 8 weight percent.

The adhesive contains 0.1 to 5, preferably 0.25 to 3, weight percent of at least one urea compound having one or more urea groups and a molecular weight per urea group of up to 250. The urea compound(s) may have the structure:

wherein n is 1 or more, R is an unsubstituted or unsubstituted alkyl, cycloalkyl and/or aromatic radical, $R^1$ is hydrogen, unsubstituted alkyl, substituted alkyl, phenyl or substituted phenyl, and each $R^2$ is independently alkyl, substituted alkyl, phenyl or substituted phenyl. R may be the residue, after removal of isocyanate groups, from a mono- or polyisocyanate compound. R may contain, for example, up to 20 carbon atoms, preferably up to 15 carbon atoms. Preferably, R, each $R^2$ and $R^1$ (if not hydrogen) are bonded to the adjacent nitrogen atom through an aliphatic carbon atom. n is preferably 1 to 4, more preferably 1, 2 or 3, and most preferably 2.

Examples of aromatic ureas include 3-phenyl-1,1-dimethylurea, 3-(p-chlorophenyl)-1,1-dimethylurea, 3-(3,4-dichlorophenyl)-1,1-dimethyl urea.

Other aromatic ureas include those corresponding to reaction products of an aromatic polyisocyanate with a dialkyl amine Examples include 2,4'- and/or 4,4'-methylene bis(phenyl dimethyl urea) and 2,4- and/or 2,6-toluene bis(dimethyl urea).

Examples of aliphatic ureas include tetraalkyl urea compounds in which the alkyl groups each independently have 1 to 12, preferably 1 to 2 carbon atoms, such as tetramethylurea and tetraethylurea.

A preferred type of aliphatic urea corresponds to a reaction product of an aliphatic (including cycloaliphatic) isocyanate with a dialkyl amine. Examples include isophorone bis(dimethyl urea), cyclohexane bis (dimethyl urea), hexane-1,6-bis(dimethyl urea), 4,4'-methylene bis(cyclohexane dimethyl urea), and the like. A commercially available isophorone bis(dimethylurea) product is Omicure™ U-35, available from Emerald Performance Materials.

In addition to improving adhesion to oily substrates (when used in conjunction with the toughener described herein) the urea compound also is believed to function as a curing accelerator, i.e., a catalyst for the curing reaction between the epoxy resin and hardener. Accordingly, it is not necessary to include a separate curing accelerator or catalyst in the adhesive composition of the invention.

However, if an additional curing accelerator is desired, it is preferably encapsulated or otherwise a latent type that becomes active only upon exposure to elevated temperatures. Examples of these include tert-acryl- or alkylene amines like benzyldimethylamine, piperidine or derivatives thereof, $C_1$-$C_{12}$ alkylene imidazole or N-arylimidazoles such as 2-ethyl-2-methylimidazol, or N-butylimidazol or 6-caprolactam. Such an additional accelerator, if present at all, may be present in an amount of 0.01 to 4 weight percent of the adhesive.

At least one type of curing accelerator, aminophenol compounds, has been found to contribute to poorer performance even when the urea compound is present. Therefore, the adhesive of the composition is devoid of aminophenol compounds.

The adhesive of the invention may contain various other, optional ingredients, in addition to those described above.

The adhesive may contain one or more mineral fillers. These can perform several functions, such as (1) modifying the rheology of the adhesive in a desirable way, (2) reducing overall cost per unit weight, (3) absorbing moisture or oils from the adhesive or from a substrate to which it is applied, and/or (4) promoting cohesive, rather than adhesive, failure. Examples of suitable mineral fillers include calcium carbonate, calcium oxide, talc, carbon black, textile fibers, glass particles or fibers, aramid pulp, boron fibers, carbon fibers, mineral silicates, mica, powdered quartz, hydrated aluminum oxide, bentonite, wollastonite, kaolin, fumed silica, silica aerogel, polyurea compounds, polyamide compounds or metal powders such as aluminum powder or iron powder. Another filler of particular interest is a microballoon having an average particle size of up to 200 microns and density of up to 0.2 g/cc. The particle size is preferably about 25 to 150 microns and the density is preferably from about 0.05 to about 0.15 g/cc. Heat expandable microballoons which are suitable for reducing density include those commercially available from Dualite Corporation under the trade designation Dualite™, and those sold by Akzo Nobel under the trade designation Expancel™.

All or part of the mineral filler may be in the form of fibers having a diameter of 1 to 50 μm (D50, as measured by microscopy) and an aspect ratio of 6 to 20. The diameter of the fibers may be 2 to 20 μm or 2 to 10 μm, and the aspect ratio may be 8 to 20 or 8 to 16. The diameter of the fiber is taken as that of a circle having the same cross-sectional area as the fiber. The aspect ratio of the fibers may be 6 or more, such as 6 to 25, 6 to 20, 8 to 20 or 8 to 15.

Alternatively, all or part of the mineral filler may be in the form of low aspect ratio particles having an aspect ratio of 5 or less and a longest dimension of up to 100 μm, preferably up to 25 μm.

The mineral filler(s) may constitute, for example, 1 to 40% of the total weight of the adhesive composition. In some embodiments, it constitutes at least 5% or at least 7.5% of the weight of the adhesive composition, and may constitute up to 25%, up to 20% or up to 15% of the weight thereof.

The adhesive may contain up to 10% by weight, preferably 1 to 6% by weight of fumed silica.

The adhesive may include a rubber component that does not include capped isocyanate groups, which is a separate material from the toughener described above. Such a rubber component is optional and can be omitted. One advantage of this invention is that excellent properties can be obtained even when the adhesive is devoid of such a component.

The optional rubber component may be, for example, a liquid rubber, preferably having two or more epoxide-reactive groups, such as amino or preferably carboxyl groups. It is preferred that at least a portion of the liquid rubber has a glass transition temperature ($T_g$) of −40° C. or lower, especially −50° C. or lower, as measured by differential scanning calorimetry. Such a liquid rubber component may be entirely or partially reacted with an epoxy resin to form a rubber-modified epoxy resin that has epoxy groups.

Such a liquid rubber is preferably a homopolymer or copolymer of a conjugated diene, especially a diene/nitrile copolymer. The conjugated diene rubber is preferably butadiene or isoprene, with butadiene being especially preferred. The preferred nitrile monomer is acrylonitrile. Preferred copolymers are butadiene-acrylonitrile copolymers. The rubbers preferably contain, in the aggregate, no more than 30 weight percent polymerized unsaturated nitrile monomer, and preferably no more than about 26 weight percent polymerized nitrile monomer. The liquid rubber preferably contains from about 1.5, more preferably from about 1.8, to about 2.5, more preferably to about 2.2, of epoxide-reactive terminal groups per molecule, on average. Carboxyl-terminated rubbers are preferred. The molecular weight ($M_n$) of the rubber is suitably from about 2000 to about 6000, more preferably from about 3000 to about 5000. Suitable carboxyl-functional butadiene and butadiene/acrylonitrile rubbers are commercially available from Noveon under the tradenames Hycar® 2000X162 carboxyl-terminated butadiene homopolymer, Hycar® 1300X31, Hycar® 1300X8, Hycar® 1300X13, Hycar® 1300X9 and Hycar® 1300X18 carboxyl-terminated butadiene/acrylonitrile copolymers. A suitable amine-terminated butadiene/acrylo-nitrile copolymer is sold under the tradename Hycar® 1300X21.

Other suitable rubbery materials include amine-terminated polyethers, fatty acids (which may be dimerized or oligomerized), and elastomeric polyester.

Another type of rubber that may be present in the adhesive composition is a core-shell rubber. The core-shell rubber is a particulate material having a rubbery core. The rubbery core preferably has a $T_g$ of less than −20° C., more preferably less than −50° C. and even more preferably less than −70° C. The $T_g$ of the rubbery core may be well below −100° C. The core-shell rubber also has at least one shell portion that preferably has a $T_g$ of at least 50° C. The core of the core-shell rubber may be a polymer or copolymer of a conjugated diene such as butadiene, or a lower alkyl acrylate such as n-butyl-, ethyl-, isobutyl- or 2-ethylhexylacrylate, or may be a silicone rubber. The shell polymer, which is optionally chemically grafted or crosslinked to the rubber core, is preferably polymerized from at least one lower alkyl methacrylate such as methyl-, ethyl- or t-butyl methacrylate. Homopolymers of such methacrylate monomers can be used. Further, up to 40% by weight of the shell polymer can be formed from other monovinylidene monomers such as styrene, vinyl acetate, vinyl chloride, methyl acrylate, ethyl acrylate, butyl acrylate, and the like. The molecular weight of the grafted shell polymer is generally between 20,000 and 500,000. Examples of useful core-shell rubbers include those described in EP 1 632 533 A1 and those sold by Kaneka Corporation under the designation Kaneka Kane Ace, including Kaneka Kane Ace MX 156 and Kaneka Kane Ace MX 120 core-shell rubber dispersions.

The total rubber content of the adhesive of the invention can range from as little as 0 weight percent to as high as 30 weight percent, based on the total weight of the adhesive. If a rubber is present at all, a preferred rubber content is up to 20 weight percent, up to 15 weight percent or up to 5 weight percent. No portion of the elastomeric toughener is considered in calculating total rubber content.

In specific embodiments, the adhesive of the invention has a total rubber content of no more than 5%, preferably no more than 1%, and more preferably no more than 0.5% by weight. The adhesive may have a rubber content of zero.

A monomeric or oligomeric, addition polymerizable, ethylenically unsaturated material is optionally present in the adhesive composition. This material should have a molecular weight of less than about 1500. This material maybe, for example, an acrylate or methacrylate compound, an unsaturated polyester, a vinyl ester resin, or an epoxy adduct of an unsaturated polyester resin. A free radical initiator can be included in the adhesive composition as well, in order to provide a source of free radicals to polymerize this material. The inclusion of an ethylenically unsaturated material of this type provides the possibility of effecting a partial cure of the adhesive through selective polymerization of the ethylenic unsaturation.

The adhesive composition can further contain other additives such as dimerized fatty acids, diluents, plasticizers, extenders, pigments and dyes, fire-retarding agents, thixotropic agents, expanding agents, flow control agents, adhesion promoters and antioxidants. Suitable expanding agents include both physical and chemical type agents. The adhesive may also contain a thermoplastic powder such as polyvinylbutyral or a polyester polyol, as described in WO 2005/118734.

The foregoing adhesive composition is formed into a layer at a bondline between two substrates to form an assembly, and the adhesive layer is cured at the bondline to form an adhesive bond between the two substrates.

The adhesive can be applied to the substrates by any convenient technique. It can be applied cold or be applied warm if desired. It can be applied manually and/or robotically, using for example, a caulking gun, other extrusion apparatus, or jet spraying methods. Once the adhesive composition is applied to the surface of at least one of the substrates, the substrates are contacted such that the adhesive is located at a bondline between the substrates.

After application, the adhesive is cured by heating it to at or above its curing temperature. Generally, this temperature is at least 60° C., and is preferably 80° C. or above, more preferably 140° C. or above. Preferably, the temperature is 180° C. or less.

The adhesive of the invention can be used to bond a variety of substrates together including wood, metal, coated metal, aluminum, a variety of plastic and filled plastic substrates, fiberglass and the like. In one preferred embodiment, the adhesive is used to bond parts of automobiles together or to bond automotive parts onto automobiles. Such parts can be steel, coated steel, galvanized steel, aluminum, coated aluminum, plastic and filled plastic substrates.

The invention has particular benefits when one or both of substrates have an oily material on a surface to which the adhesive is applied. By "oily material", it is meant an electrostatically neutral, hydrophobic material that has a melting temperature of 40° C. or lower and a viscosity of at least 5 centistokes (5 mm$^2$/s) at 40° C. as measured by ASTM D445. The viscosity may be, for example, at least 8 centistokes, at least 20 centistokes or at least 50 centistokes to as much as 500 centistokes, as much as 250 centistokes or as much as 125 centistokes at that temperature. By "hydrophobic", it is meant the material is soluble in water to the extent of no more than 2 parts by weight per 100 parts by weight water at 23° C. The oily material may include, for example, a petroleum product, a plant or animal oil or fat, and/or a synthetic oil such as various types of synthetic ester lubricants. Examples of oily materials include for example, lubricating oils such as sewing machine oils, stamping oils, motor oils, soldering pastes, gear lubricants, die lubricants, trim press lubricants, and aviation oils, axle and transmission oils, compressor oils, electrical oils, gear oils, hydraulic fluids, process oils, slideway oils and turbine oils. Such oils include those sold, for example, by Fuchs Lubricants UK PLC, International Chemical Company, Philadelphia, Pa., USA, Chemtool Inc., Rockland, Ill., USA, and Lamson Oil Co., Rockland, Ill., USA, among many others. A specific example is Anticorit™ PL3802-3S from Fuchs Lubricants UK. The oily material may contain various types of contaminants. The amount of oil on the surface of the substrate to which the adhesive is applied may be, for example 0.1 to 10 g/m$^2$, 0.25 to 5 g/m$^2$, or 0.5 to 2.5 g/m$^2$.

The excellent wash-off resistance of adhesive of the invention is particularly beneficial when one or both of the substrates is coated at the time the adhesive is applied to the substrate with an oil having a viscosity of at least 50 mm$^2$/s at 40° C. In some manufacturing processes, the oil coating is removed in a washing step (commonly referred to as "degreasing") that takes place after the adhesive is applied and before it is cured. When higher viscosity oils are present, the washing temperature is often increased to 40° C. or more, or 50° C. or more, to facilitate removal of the oil. These higher washing temperatures require the adhesive to be highly resistant to washing off, so it is not removed with the oil; therefore the wash-off resistance of the inventive adhesive is of particular value in cases in which a step of washing off (degreasing) an oil coating is performed at a temperature of at least 40° C. or at least 50° C. after the adhesive is applied but before it has been cured.

An application of particular interest is bonding of automotive frame components to each other or to other components. The frame components are often metals such as cold rolled steel, galvanized metals, or aluminum, which are frequently contaminated with an oil as described above. The components that are to be bonded to the frame components can also be metals as just described, or can be other metals, plastics, composite materials, and the like.

Assembled automotive frame members are usually coated with a coating material that requires a bake cure. The coating is typically baked at temperatures that may range from 140° C. to over 200° C. In such cases, it is often convenient to apply the adhesive to the frame components (which may be coated with an oil as described above), then apply the coating, and cure the adhesive at the same time the coating is baked and cured. Between the steps of applying the adhesive and applying the coating, the assembly may be fastened together to maintain the substrates and adhesive in a fixed position relative to each other, until the curing step is performed. Mechanical means can be used as a fastening device. These include, for example, temporary mechanical means such as various types of clamps, bands and the like, which can be removed once the curing step is completed. The mechanical fastening means can be permanent, such as, for example, various types of welds, rivets, screws, and/or crimping methods. Alternatively or in addition, the fastening can be done by spot-curing one or more specific portions of the adhesive composition to form one or more localized adhesive bonds between the substrates while leaving the remainder of the adhesive uncured until a final curing step is performed after the coating is applied.

The following examples are provided to illustrate the invention but are not intended to limit the scope thereof. All parts and percentages are by weight unless otherwise indicated. All molecular weights are number averages unless otherwise indicated.

In the following examples:

Epoxy Resin A is a liquid diglycidyl ether of bisphenol A, having an epoxy equivalent weight of about 187.

Epoxy Resin B is a mixture of solid and liquid diglycidyl ethers of bisphenol A. The mixture has an epoxy equivalent weight of about 240.

Epoxy Resin C is an epoxy novolac resin having an epoxy equivalent weight of about 179.

Epoxy Resin D is an epoxy-functional diluent.

Toughener A is an elastomeric toughener containing blocked isocyanate groups. It is prepared by mixing 54.79 parts of a 2000 molecular weight polytetrahydrofuran and 13.67 parts of a 2800 molecular weight, hydroxyl-terminated polybutadiene polymer at 120° C., cooling the mixture to 60° C., adding 15.09 parts of isophorone diisocyanate and a tin urethane catalyst and heating the resulting reaction mixture to 85° C. for 45 minutes under nitrogen. Then, 5.74 parts of o,o'-diallylbisphenol A are added, and the mixture is stirred for 120 minutes under vacuum in a 100° C. bath. 10.65 parts of cardanol are then added and the mixture is stirred for another 240 minutes under vacuum in a 105° C. bath.

Toughener B is an elastomeric toughener containing blocked isocyanate groups. It is prepared by mixing 57.58 parts of a 2000 molecular weight polytetrahydrofuran and 14.39 parts of a 2800 molecular weight hydroxyl-terminated polybutadiene polymer at 120° C., cooling the mixture to 60° C., adding 11.54 parts of hexamethylene diisocyanate and a tin urethane catalyst and heating the resulting reaction mixture to 85° C. for 45 minutes under nitrogen. Then, 5.74 parts of o,o'-diallylbisphenol A are added, and the mixture is stirred for 120 minutes under vacuum in a 100° C. bath. 10.58 parts of cardanol are added and the mixture is stirred for 240 minutes under vacuum in a 105° C. bath.

Toughener C is an elastomeric toughener having capped isocyanate groups sold as Struktol™ 3604 by Struktol Company of America.

The Core-Shell Rubber is a dispersion of core-shell rubber particles in an epoxy resin, sold as Kane Ace MX 156 by Kaneka Corporation.

Urea A is a 4,4'-methylene bis (phenyl dimethyl urea), commercially available as Omicure U-52 from Emerald Performance Products.

Urea B is isophorone bis(dimethylurea), commercially available as Omicure U-35 from Emerald Performance Products.

Urea C is tetramethylurea.

EP796 is tris(2,4,6-dimethylaminomethyl)phenol in a poly(vinylphenol) matrix.

Examples 1 and 2 and Comparative Samples A and B

Adhesive Examples 1 and 2 and Comparative Samples A and B are prepared by blending ingredients as indicated in Table 1:

TABLE 1

| Component | Parts By Weight | | | |
|---|---|---|---|---|
| | Ex. 1 | Ex. 2 | Comp. Samp. A | Comp. Samp. B |
| Epoxy Resin A | 28.44 | 28.44 | 28.44 | 34 |
| Epoxy Resin B | 17 | 17 | 17 | 14.19 |
| Epoxy Resin C | 3 | 3 | 3 | 0 |

TABLE 1-continued

| | Parts By Weight | | | |
|---|---|---|---|---|
| Component | Ex. 1 | Ex. 2 | Comp. Samp. A | Comp. Samp. B |
| Toughener A | 19.0 | 19.0 | 19.0 | 19.0 |
| 3-glycidyloxypropyl-triethoxysilane | 0.61 | 0.61 | 0.61 | 0.61 |
| Surfactant | 0.28 | 0.28 | 0.28 | 0.28 |
| Colorant | 0.35 | 0.35 | 0.35 | 0.35 |
| Dicyanamide | 5.17 | 5.17 | 5.15 | 5.22 |
| Urea A | 0 | 0.7 | 0.5 | 0 |
| Urea B | 0.7 | 0 | 0 | 0 |
| EP796 | 0 | 0 | 0.3 | 0.7 |
| Hydrophobic Fumed Silica | 7.0 | 7.0 | 7.0 | 7.2 |
| Calcium Carbonate | 10 | 10 | 10 | 10 |
| Calcium Oxide | 6.5 | 6.5 | 6.5 | 6.0 |
| Talc | 0.2 | 0.2 | 0.2 | 0.2 |
| Glass Microspheres | 1.75 | 1.75 | 1.75 | 2.25 |

Test samples for tensile strength, elongation and elastic modulus measurements are made by curing a portion of each sample for 30 minutes at 180° C. Test specimens are cut from the cured samples and evaluated according to DIN EN ISO 527-1.

Impact peel testing is performed for each adhesive sample. The test coupons for the impact peel testing are 90 mm×20 mm with a bonded area of 30×20 mm. The adhesive sample is then applied to the bond area of a 1.2 mm-thick HC420LAD+Z100 hot dipped zinc coated steel coupon. A 1.2 mm-thick HC340LAD+ZE 50-50 electrolytically zinc coated coupon is placed into contact with the adhesive, and the assembly squeezed under a weight of about 10 kg to prepare each test specimen, with spacers present to maintain an adhesive layer thickness of 0.2 mm. The assembled test specimens are cured at 180° C. for 30 minutes. The impact peel testing is performed in accordance with the ISO 11343 wedge impact method. Testing is performed at an operating speed of 2 m/sec with samples at a temperature of 23° C.

Lap shear specimens are made using coupons of the same materials. The specimens are made by sprinkling glass beads (0.2 mm diameter) onto one of the coupons, applying the adhesive sample, and then positioning the second coupon on top of the adhesive. The bonded area in each case is 25×10 mm, and the adhesive layer thickness is controlled by the glass beads to 0.2 mm. The test specimens are cured for 30 minutes at 180° C. and evaluated for lap shear strength in accordance with DIN ISO 1465. Testing is performed at 23° C. and a test speed of 10 mm/minute.

Viscosity and yield stress are measured on a Bohlin CS-50 rheometer, C/P 20, up/down 0.1-20 s$^{-1}$, with data evaluated according to the Casson model.

A tack test is performed to evaluate the ability of each adhesive to penetrate an oily coating. Two 40×125 mm metal coupons are coated with about 1.8 g/m$^2$ of a petroleum-based stamping oil that has a kinematic viscosity of 60 centistokes at 40° C. (Anticorit PL3802-39S from Fuchs Lubricants). Each adhesive samples is blended with 2 weight percent 0.2 mm glass beads to act as spacers. The adhesive is applied over the surface of one of the coupons. The other coupon is laid on top of the adhesive, and the assembly squeezed under an applied weight of about 10 kg. After 30 minutes at room temperature, the coupons are manually separated, and inspected for the distribution of the adhesive between the coupons. The desired result is that the adhesive is distributed evenly between the coupons after they are separated, as this indicates a good ability for the adhesive to penetrate through the oil layer.

Figure 1B:
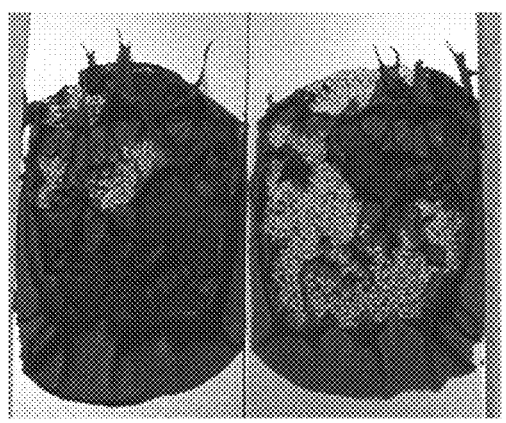
FIG. 1B is a photograph of separated oily metal substrates with applied adhesive, which demonstrates adequate performance on the tack test described below.
Figure 1C:
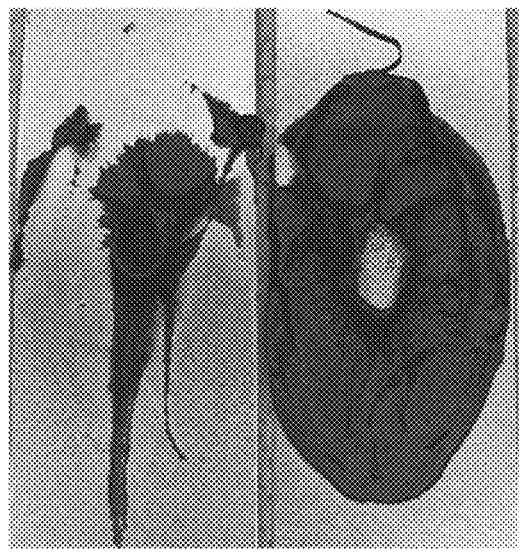
FIG. 1C is a photograph of separated oily metal substrates with applied adhesive, which demonstrates poor performance on the tack test described below.

The distribution of the adhesive on the separated coupons is rated as "excellent", "adequate" or "poor". An "excellent" rating means the adhesive is distributed essentially between the separated coupons, with few if any areas where the adhesive has been pulled away from either coupon. A sample of an "excellent rating" is shown in FIG. 1A. An "adequate" rating means that although there is some adhesive on each of the separated coupons, there are significant areas (10 to 60% of the total contact area of the adhesive with the coupon) from at least one of the coupons where the adhesive has become pulled away. A sample of an "adequate" rating is shown in FIG. 1B. A "poor" rating means that the adhesive is pulled away from at least one of the coupons at more than 60% of the surface area to which it is applied. A sample of a "poor" rating is shown in FIG. 1C.

Wash-off testing is performed by applying an adhesive bead to a 200×40 mm metal panel. A smaller (150×20 mm) panel is placed on top of the adhesive bead, and five punch rivets are set along the length of the assembly at a regular distance of 27 mm. During the riveting process, a portion of the adhesive is squeezed out from under the smaller panel and becomes exposed. Triplicate samples are produced with each adhesive. The samples are vertically mounted to a stirrer and rack assembly. The rack assembly is immersed in 60° C. water and rotated at 140 rpm for three minutes. The test samples are oriented on the stirred and rack assembly so they move edge-on through the water as the stirred rotates. The samples are then removed from the water, and the exposed portion of the adhesive is examined visually.

Wash-off is indicated by the deformation of the exposed area of the adhesive layer, particularly at the edges where it tends to become separated from the surface of the larger metal coupon. If no material deformation occurs, the sample is accorded an "excellent" rating. Samples with only minor deformation of the adhesive are rated as "good". Samples in which the edges of the exposed adhesive layer are ruptured and have begun to wash onto the exposed surface of the smaller panel are rated "fair". A "poor" rating indicates substantial wash-off, with significant loss of material and/or washing of significant portions of the adhesive onto the exposed surface of the smaller panel.

Results of the various testing are as indicated in Table 2.

TABLE 2

| Designation | Ex. 1 | Ex. 2 | Comp. Samp. A | Comp. Samp. B |
|---|---|---|---|---|
| Accelerator | Urea B | Urea A | Urea A/EP 796 | EP 796 |
| Property | | | | |
| Elastic Modulus, MPa | 1800 | 2020 | N.D. | 1940 |
| Tensile Strength, MPa | 33 | 34 | N.D. | 33 |
| Elongation at Break, % | 3.6 | 3.8 | N.D. | 3.4 |
| Impact Peel Str., N/mm | 25 | 27 | N.D. | 26.0 |
| Lap Shear Str., MPa | 33 | 31.4 | 32.2 | 32.9 |
| Yield stress, 45° C., Pa | 880 | 950 | 675 | 600 |
| Viscosity, 45° C., Pa · s | 77 | 77 | 89 | 67 |
| Tack Test Rating | Excellent | Excellent | Poor | Poor |
| Wash-off Test Rating | Excellent | Excellent | Fair | Fair |

Examples 1 and 2 both exhibit excellent results on the tack and wash off tests. Comparative Sample A is made from essentially the same formulation as Examples 1 and 2, except part of the urea is replaced with an aminophenol. Despite the presence of both the urea and the chain-extended toughener, the tack test rating falls to poor, indicating an inability of this adhesive to penetrate through an oily coating on the substrate. Comparative Sample B is a slightly different formulation that when cured exhibits adhesive and mechanical properties very similar to those of Examples 1 and 2. However, Comparative Sample B contains the aminophenol accelerator and no urea. Its wash-off rating is only fair and the tack test rating is poor.

These examples demonstrate the very substantial effect of the selection of curing accelerator on the ability of the adhesive to penetrate an oily coating and to resist wash-off. These results are particularly surprising in view of the very small quantity of accelerator in the formulations; the curing accelerator constitutes less than 1% of each of these formulations.

Examples 3-5 and Comparative Samples C and D

Adhesive Examples 3 through 5 and Comparative Samples C and D are prepared by blending ingredients as indicated in Table 3:

TABLE 3

|  | Parts By Weight | | | | |
| --- | --- | --- | --- | --- | --- |
| Component | Ex. 3 | Ex. 4 | Ex. 5 | Comp. Samp. C | Comp. Samp. D |
| Epoxy Resin A | 30.03 | 30.03 | 28.30 | 28.41 | 33.88 |
| Epoxy Resin B | 18 | 18 | 20 | 15 | 15 |
| Epoxy Resin C | 3 | 3 | 3 | 0 | 0 |
| Toughener B | 17 | 17 | 17 | 20 | 19 |
| Toughener C | 0 | 0 | 0 | 5 | 0 |
| 3-glycidyloxypropyl-triethoxysilane | 0.61 | 0.61 | 0.61 | 0.61 | 0.61 |
| Surfactant | 0.28 | 0.28 | 0.28 | 0.28 | 0.28 |
| Colorant | 0.35 | 0.35 | 0.4 | 0.35 | 0.35 |
| Dicyanamide | 4.83 | 4.83 | 4.81 | 5.00 | 5.33 |
| Urea A | 0.7 | 0.35 | 0 | 0 | 0 |
| Urea B | 0 | 0.35 | 0.7 | 0 | 0 |
| EP796 | 0 | 0 | 0 | 0.7 | 0.7 |
| Hydrophobic Fumed Silica | 6.5 | 6.5 | 6.2 | 6.4 | 6.4 |
| Calcium Carbonate | 10 | 10 | 10 | 10 | 10 |
| Calcium Oxide | 6.5 | 6.5 | 6.5 | 6.0 | 6.0 |
| Talc | 0.2 | 0.2 | 0.2 | 0.2 | 0.2 |
| Glass Microspheres | 2 | 2 | 2 | 2.25 | 2.25 |

These adhesives are evaluated as described in the preceding example. Results are as indicated in Table 4:

TABLE 4

| Designation | Ex. 3 | Ex. 4 | Ex. 5 | Comp. Samp. C | Comp. Samp. D |
| --- | --- | --- | --- | --- | --- |
| Accelerator | Urea A | Urea A / Urea B | Urea B | EP 796 | EP 796 |
| Property | | | | | |
| Elastic Modulus, MPa | 1780 | 1810 | 1870 | 1580 | 1840 |
| Tensile Strength, MPa | 31 | 33 | 33 | 28 | 33 |
| Elongation at Break, % | 4.2 | 4.6 | 4.4 | 4.2 | 3.9 |
| Impact Peel Str., N/mm | 27 | 25 | 25 | 33 | 27 |
| Lap Shear Str., MPa | 32.3 | 30.4 | 33.7 | 29.2 | 31.2 |
| Yield stress, 45° C., Pa | 681 | 706 | 763 | 607 | 675 |
| Viscosity, 45° C., Pa · s | 88 | 84 | 72 | 113 | 89 |
| Tack Test Rating | Excellent | Excellent | Excellent | Poor | Poor |
| Wash-off Test Rating | Excellent | Excellent | Excellent | Fair | Fair |

The data in Table 4 again shows the large and unexpected effect of curing agent on tack test rating. The aminophenol has a large adverse affect, whereas the urea curing agents produce adhesives that perform excellently on the tack test. Other properties are largely unchanged across this set of adhesives.

Examples 6-8

Adhesive Examples 6 through 8 are prepared by blending ingredients as indicated in Table 5:

TABLE 5

|  | Parts By Weight | | |
| --- | --- | --- | --- |
| Component | Ex. 6 | Ex. 7 | Ex. 8 |
| Epoxy Resin A | 24.62 | 30.03 | 22.56 |
| Epoxy Resin B | 24 | 18 | 27 |
| Epoxy Resin C | 3 | 3 | 3 |
| Toughener A | 17 | 17 | 17 |
| 3-glycidyloxypropyltriethoxysilane | 0.61 | 0.61 | 0.61 |
| Surfactant | 0.28 | 0.28 | 0.28 |
| Colorant | 0.35 | 0.35 | 0.35 |
| Dicyanamide | 4.74 | 4.83 | 4.75 |
| Urea A | 0.35 | 0.7 | 0.5 |
| Urea B | 0.35 | 0 | 0 |
| Tetramethylurea | 0 | 0 | 1.0 |
| Hydrophobic Fumed Silica | 6.0 | 6.5 | 7.5 |
| Calcium Carbonate | 10 | 10 | 10 |
| Calcium Oxide | 6.5 | 6.5 | 6.5 |
| Talc | 0.2 | 0.2 | 0.2 |
| Glass Microspheres | 2 | 2 | 1.75 |

These adhesives are evaluated as described in the preceding example. Results are as indicated in Table 6:

TABLE 6

| Designation | Ex. 6 | Ex. 7 | Ex. 8 |
| --- | --- | --- | --- |
| Accelerator | Urea A / Urea B | Urea A | Urea A / TMU |
| Property | | | |
| Elastic Modulus, MPa | 1950 | 2050 | 1980 |
| Tensile Strength, MPa | 36 | 35 | 36 |
| Elongation at Break, % | 4.3 | 3.9 | 3.8 |
| Impact Peel Str., N/mm | 24 | 24 | 27 |
| Lap Shear Str., MPa | 34.2 | 31.8 | 34.7 |
| Yield stress, 45° C., Pa | 630 | 725 | 877 |
| Viscosity, 45° C., Pa · s | 81 | 72 | 67 |
| Tack Test Rating | Excellent | Excellent | Adequate |
| Wash-off Test Rating | Excellent | Excellent | Good |

As before, the selection of the chain-extended toughener in conjunction with urea accelerators leads to adequate or better results in the tack test and good or better results in the wash-off test, when no aminophenol is present. Ex. 8 demonstrates that the substitution of tetramethyl urea (TMU) for a part of Urea A leads to some loss in tack test and wash-off resistance, although the performance of that sample is till considered to be generally good.

Comparative Samples E and F

Comparative Samples E and F are prepared by blending ingredients as indicated in Table 7. Toughener C is an amine-capped toughener prepared according to Example 2 of U.S. Pat. No. 8,404,787. Toughener D is a bis-phenol A capped toughener described as Toughener B in WO 2005/007766. Neither Toughener C nor Toughener D is chain extended, and neither is formed from an isocyanate-terminated butadiene polymer.

TABLE 7

| Component | Parts By Weight | |
|---|---|---|
| | Comp. Sample E | Comp. Sample F |
| Epoxy Resin A | 19.0 | 0 |
| Epoxy Resin B | 30 | 48.8 |
| Epoxy Resin C | 3 | 3 |
| Toughener C | 0 | 17 |
| Toughener D | 17 | 0 |
| 3-glycidyloxypropyltriethoxysilane | 0.61 | 0.61 |
| Surfactant | 0.28 | 0.28 |
| Colorant | 0.35 | 0.35 |
| Dicyanamide | 4.6 | 4.6 |
| Urea B | 0.7 | 0.7 |
| Hydrophobic Fumed Silica | 6.0 | 6.0 |
| Calcium Carbonate | 10 | 10 |
| Calcium Oxide | 6.5 | 6.5 |
| Talc | 0.2 | 0.2 |
| Glass Microspheres | 2 | 2 |

These adhesives are evaluated as described in the preceding example. Results are as indicated in Table 8:

TABLE 8

| Designation | Comp. Sample E | Comp. Sample F |
|---|---|---|
| Property | | |
| Elastic Modulus, MPa | 2110 | 1930 |
| Tensile Strength, MPa | 38 | 34 |
| Elongation at Break, % | 3.7 | 3.8 |
| Lap Shear Str., MPa | 36 | 34 |
| Yield stress, 45° C., Pa | 613 | 557 |
| Viscosity, 45° C., Pa · s | 96 | 78 |
| Tack Test Rating | Poor | Poor |
| Wash-off Test Rating | Poor | Poor |

The tack test and wash-off results demonstrate the need for the simultaneous selection of toughener and curing accelerator. Although these samples are cured with a urea curing accelerator, and contain no aminophenol, they nonetheless perform poorly on the tack and wash-off tests. These poorer results are attributed to the selection of the different tougheners. The selection of toughener has a particularly large impact on wash-off test results.

The invention claimed is:

1. A method for adhering a first oily substrate to a second substrate, comprising
   1) forming a layer of a one-component epoxy adhesive comprising in admixture:
   A) at least 25 weight percent, based on the weight of the adhesive, of one or more non-rubber-modified epoxy resins;
   B) 5 to 45 weight percent, based on the weight of the composition, of a reactive elastomeric toughener having capped isocyanate groups, which reactive elastomeric toughener includes a chain-extended and then isocyanate-capped mixture of i) a 1000 to 10,000 number average molecular weight isocyanate-terminated polyether and ii) a 1000 to 10,000 number average molecular weight isocyanate-terminated diene polymer;
   C) one or more latent epoxy curing agents in an amount sufficient to cure the adhesive; and
   D) 0.1 to 5 weight percent, based on the weight of the adhesive, of at least one urea compound having one or more urea groups and a molecular weight per urea group of up to 250, the adhesive being devoid of an aminophenol curing accelerator,
   at a bondline between the first oily substrate and the second substrate to form an assembly that includes the first and second substrates each in contact with the adhesive composition at the bondline; then
   2) degreasing the assembly to remove oil from the first oily substrate; and then
   3) heating the degreased assembly to an elevated temperature to cure the adhesive.

2. The method of claim 1, wherein the urea compound is polyurea corresponding to a reaction product of an aromatic polyisocyanate with a dialkyl amine.

3. The method of claim 2, wherein the urea compound corresponds to a reaction product of an aliphatic polyisocyanate with a dialkyl amine.

4. The method of claim 3 wherein the urea compound is isophorone bis(dimethyl urea).

5. The method of claim 2 wherein the urea compound is one or more of 2,4'- and/or 4,4'-methylene bis(phenyl dimethyl urea) and 2,4- and/or 2,6-toluene bis(dimethyl urea).

6. The method of claim 1, wherein the latent epoxy curing agent includes dicyanamide.

7. The method of claim 1, wherein the toughener is made in a process that includes the steps of chain-extending the mixture of the isocyanate-terminated polyether and the isocyanate-terminated diene polymer and then capping the remaining isocyanate groups of the chain-extended material.

8. The method of claim 1, wherein the isocyanate groups of the isocyanate-terminated polyether and the isocyanate-terminated diene polymer are aliphatic isocyanate groups.

9. The method of claim 1, wherein the capped isocyanate groups of the toughener are capped with a monophenol or an aminophenol.

10. The method of claim 1 which further comprises the steps of:
1-A): after step 1) and before step 2), fastening the assembly using mechanical means, by spot-curing one or more portions of the adhesive composition, or both, to maintain the substrates and adhesive in a fixed position relative to each other, wherein at least a portion of the adhesive remains uncured; and
2-A): after step 2) and before step 3), contacting the fastened assembly with a heat-curable coating to form a coated and fastened assembly.

11. The method of claim 10 wherein the heat-curable coating is cured in step 3).

12. The method of claim 10 or 11, wherein the degreasing step 2) is performed at a temperature of at least 50° C.

* * * * *